United States Patent
Wu et al.

(10) Patent No.: US 10,781,468 B2
(45) Date of Patent: *Sep. 22, 2020

(54) METHOD FOR PRODUCING GLUCOSAMINE

(71) Applicant: YUAN ZE UNIVERSITY, Taoyuan (TW)

(72) Inventors: Ho-Shing Wu, Taoyuan (TW); Jian-Hao Chen, Taoyuan (TW)

(73) Assignee: YUAN ZE UNIVERSITY, Taoyuan (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/794,857

(22) Filed: Oct. 26, 2017

(65) Prior Publication Data

US 2018/0119190 A1   May 3, 2018

(30) Foreign Application Priority Data

Oct. 27, 2016   (TW) .............................. 105134738 A

(51) Int. Cl.
| | |
|---|---|
| C12P 19/26 | (2006.01) |
| C12N 1/14 | (2006.01) |
| C12N 1/32 | (2006.01) |
| C07K 1/00 | (2006.01) |
| C12P 1/02 | (2006.01) |

(52) U.S. Cl.
CPC ................. *C12P 19/26* (2013.01); *C12N 1/14* (2013.01); *C12N 1/32* (2013.01); *C07K 1/00* (2013.01); *C12P 1/02* (2013.01)

(58) Field of Classification Search
CPC ... C12P 19/26; C12P 1/02; C12N 1/14; C12N 1/32; C07K 1/00
USPC .......................... 435/71.1, 171, 254.1, 256.8
See application file for complete search history.

(56) References Cited

U.S. PATENT DOCUMENTS

2010/0240105 A1*  9/2010  Wu .................. C12P 19/26
                                               435/128
2018/0016608 A1*  1/2018  Zou .................. C12R 1/125

OTHER PUBLICATIONS

Wang et al. Enhanced Glucosamine Production With Actinomucor Elegans Based on Stimulating Factor of Methanol; Indian Journal of Microbiology, vol. 54, No. 4, pp. 459-465. (Year: 2014).*
Chen et al. Optimization of Glucose Feeding Approaches for Enhanced Glucosamine and N-Acetylglucosamine Production by an Engineered *Escherichia Coli*; Journal of Industrial Microbiology and Biotechnology, vol. 39, pp. 359-365. (Year: 2012).*
Firestone et al. Fungal Toxicity of Mobilized Soil Aluminum and Manganese; Applied and Environmental Microbiology; vol. 46, No. 3, pp. 758-761. (Year: 1983).*
Pina et al. Microbial Interactions With Aluminum; Biometals, vol. 9, No. 3, Abstract. (Year: 1996).*
Chang et al. Optimizing Biotechnological Production of Glucosamine As Food Ingredient From Aspergillus SP. BCRC31742; Journal of Food Technology, vol. 9, No. 2, pp. 75-82. (Year: 2011).*

* cited by examiner

*Primary Examiner* — Juliet C Switzer
*Assistant Examiner* — Paul C Martin
(74) *Attorney, Agent, or Firm* — Muncy, Geissler, Olds & Lowe, P.C.

(57) ABSTRACT

The invention relates to a medium for producing glucosamine, including 25-500 g/L molasses, 0.01-100 g/L soybean hydrolysate or 0.25-100 g/L corn steep liquor, 0.1-2 g/L $MgSO_4 \cdot 7H_2O$, 0.1-0.5 g/L $Al(NO_3)_3$, and 1-5 mL/L methanol. The invention also relates to a method for producing glucosamine, including providing microorganism being able to produce glucosamine, and fermenting the microorganism in the medium mentioned above.

1 Claim, 6 Drawing Sheets

METHOD FOR PRODUCING GLUCOSAMINE

BACKGROUND OF THE INVENTION

1. Field of the Invention

The present invention relates to a medium for producing glucosamine, particularly to a medium using molasses as a carbon source and using soybean hydrolysate or corn steep liquor as a nitrogen source to reduce production costs and increase yields of glucosamine, and application of the medium.

2. Description of the Prior Art

Glucosamine is one of the key components of cartilage and has been extensively used to treat osteoarthritis and rheumatoid arthritis. It has also been proven that glucosamine inhibits the proliferation and induces apoptosis of leukemia cells. In addition, glucosamine possesses natural anti-inflammatory and anti-aging properties. Glucosamine is deemed to be a natural and harmless compound and therefore is widely used as food supplements in some countries in Europe and America.

There are three major ways to produce glucosamine: acid hydrolysis, enzymatic hydrolysis, and microbial fermentation. Traditionally, glucosamine is derived from hydrolysis of chitin and/or chitosan by strong acids (such as hydrochloric acid and nitric acid), which causes problems of acid waste treatment.

Enzymatic hydrolysis of chitin and chitosan to produce glucosamine causes fewer problems about waste treatment. There are many options of enzymes for producing glucosamine, and the most commonly used ones include chitinase and chitosanase. However, in addition to the high prices of the enzymes, enzymatic hydrolysis efficiency is quite low due to the poor water-solubility of chitin and chitosan. Therefore, enzymatic production of glucosamine still cannot be commercialized due to high production costs and low yields.

At present, industrial production of glucosamine is mainly carried out by acid hydrolysis of shrimp and crab shells. However, the sources of the shells may affect the purity of glucosamine, and glucosamine produced from contaminated shells may be toxic. Furthermore, washing shrimp and crab shells to prevent stink before hydrolysis and additional purification processes to remove other by-products that may cause allergies in humans are both time consuming and increase production costs. Based on all the disadvantages described above, production of glucosamine by microorganisms may be a better option than traditional acid hydrolysis.

In addition to acid and enzymatic hydrolysis, specific microorganisms can produce glucosamine as well. Compared to hydrolysis, production of glucosamine by microorganisms is not limited by reactors or the source of raw materials, has short production cycle time, provides glucosamine consistently, and causes very few environmental problems. In addition, glucosamine produced by microbial fermentation is free from stinks and heavy metal contamination and does not cause allergies in humans. Therefore, production of glucosamine by microorganisms is drawing more and more attention of researchers. However, low yields and high production costs of glucosamine produced by microbial fermentation are still some problems that need to be solved. Therefore, it is important to develop media for producing glucosamine to increase yields and reduce production costs of glucosamine.

SUMMARY OF THE INVENTION

The first aspect of the present invention relates to a medium for producing glucosamine, comprising
25-500 g/L molasses;
0.01-100 g/L soybean hydrolysate or 0.25-100 g/L corn steep liquor;
0.1-2 g/L $MgSO_4.7H_2O$;
0.1-0.5 g/L $Al(NO_3)_3$; and
1-5 mL/L Methanol.

The second aspect of the present invention relates to a method for producing glucosamine, comprising:
providing a microorganism being able to produce glucosamine; and
fermenting the microorganism in a medium comprising:
25-500 g/L molasses;
0.01-100 g/L soybean hydrolysate or 0.25-100 g/L corn steep liquor;
0.1-2 g/L $MgSO_4.7H_2O$;
0.1-0.5 g/L $Al(NO_3)_3$; and
1-5 mL/L Methanol.

These and other aspects of the present invention will become apparent from the following description of the preferred embodiment taken in conjunction with the following drawings, although variations and modifications therein may be effected without departing from the spirit and scope of the novel concepts of the disclosure.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment, and wherein.

DETAILED DESCRIPTION OF THE PREFERRED EMBODIMENT

Figure 1:
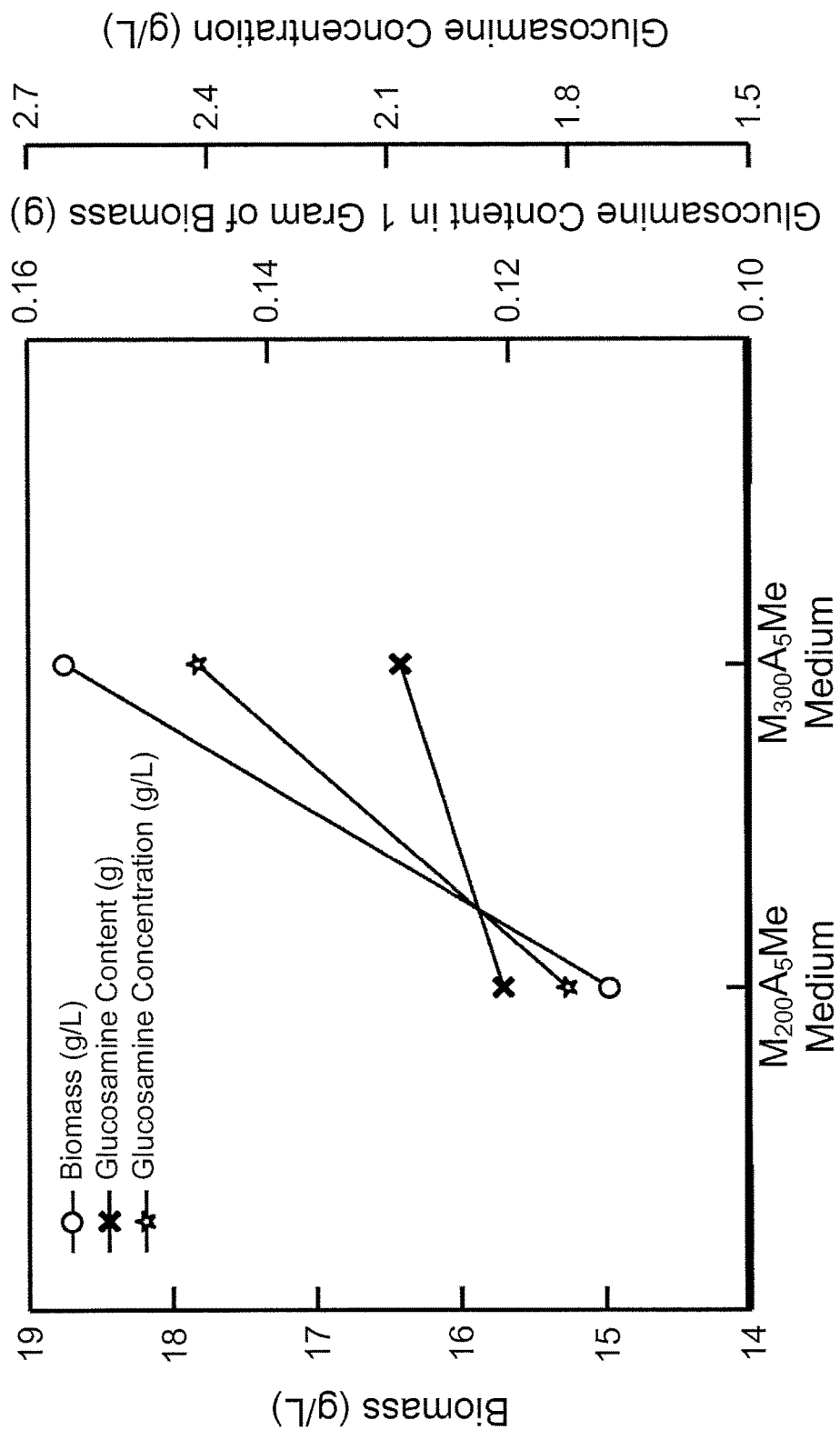
FIG. 1 shows the biomass, glucosamine concentration, and glucosamine content of *Aspergillus sydowii* BCRC 31742 cultivated in media containing different concentrations of molasses in shake flasks.

The invention provides a medium for producing glucosamine with low costs. The medium uses molasses as a carbon source and uses soybean hydrolysate or corn steep liquor as a nitrogen source. The medium comprises 25-500 g/L molasses, 0.01-100 g/L soybean hydrolysate or 0.25-100 g/L corn steep liquor, 0.1-2 g/L $MgSO_4.7H_2O$, 0.1-0.5 g/L $Al(NO_3)_3$, and 1-5 mL/L methanol.

In some embodiments, the molasses is pretreated with the following steps: mixing a molasses stock with water at a ratio of 0.5:1 to 5:1 by volume, allowing the mixed molasses stock and water to settle and form a upper layer and a lower layer, and collecting the upper layer as treated molasses. In some preferred embodiments, the molasses stock is mixed with water at a ratio of 0.5:1, 1:1, 1.5:1, 2:1, 2.5:1, 3:1, 3.5:1, 4:1, 4.5:1, or 5:1 by volume.

In some embodiments, the concentration of molasses is 25-500 g/L. In some preferred embodiments, the concentration of molasses is 25, 30, 40, 50, 60, 70, 80, 90, 100, 125, 150, 175, 200, 225, 250, 275, 300, 325, 350, 375, 400, 425, 450, 475, or 500 g/L.

In some embodiments, the concentration of soybean hydrolysate is 0.01-100 g/L. In some preferred embodiments, the concentration of soybean hydrolysate is 0.01, 0.05, 0.1, 0.25, 0.5, 0.75, 1, 5, 10, 15, 20, 25, 30, 35, 40, 45, 50, 55, 60, 65, 70, 75, 80, 85, 90, 95, or 100 g/L.

In some embodiments, the concentration of corn steep liquor is 0.25-100 g/L. In some preferred embodiments, the concentration of corn steep liquor is 0.25, 0.50, 0.75, 1, 5, 10, 15, 20, 25, 30, 35, 40, 45, 50, 55, 60, 65, 70, 75, 80, 85, 90, 95, or 100 g/L.

In some embodiments, the concentration of $MgSO_4.7H_2O$ is 0.1-2 g/L. In some preferred embodiments, the concentration of $MgSO_4.7H_2O$ is 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2 g/L.

In some embodiments, the concentration of $Al(NO_3)_3$ is 0.1-0.5 g/L. In some preferred embodiments, the concentration of $Al(NO_3)_3$ is 0.1, 0.2, 0.3, 0.4, or 0.5 g/L.

In some embodiments, the concentration of methanol is 1-5 mL/L. In some preferred embodiments, the concentration of methanol is 1, 1.1, 1.2, 1.3, 1.4, 1.5, 1.6, 1.7, 1.8, 1.9, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.95 mL/L.

The invention further provides a method for producing glucosamine, comprising: providing a microorganism being able to produce glucosamine; and fermenting the microorganism in a medium containing molasses; wherein the medium comprises 25-500 g/L molasses, 0.01-100 g/L soybean hydrolysate or 0.25-100 g/L corn steep liquor, 0.1-2 g/L $MgSO_4.7H_2O$, 0.1-0.5 g/L $Al(NO_3)_3$, and 1-5 mL/L methanol.

In some embodiments, the microorganism being able to produce glucosamine includes, but not is limited to, *Absidia coerulea*, *Aspergillus sydowii*, and *Mucor indicus*.

In some embodiments, the molasses is pretreated with the following steps: mixing a molasses stock with water at a ratio of 0.5:1 to 5:1 by volume, allowing the mixed molasses stock and water to settle and form a upper layer and a lower layer, and collecting the upper layer as treated molasses. In some preferred embodiments, the molasses stock is mixed with water at a ratio of 0.5:1, 1:1, 1.5:1, 2:1, 2.5:1, 3:1, 3.5:1, 4:1, 4.5:1, or 5:1 by volume.

In some embodiments, the concentration of molasses is 25-500 g/L. In some preferred embodiments, the concentration of molasses is 25, 30, 40, 50, 60, 70, 80, 90, 100, 125, 150, 175, 200, 225, 250, 275, 300, 325, 350, 375, 400, 425, 450, 475, or 500 g/L.

In some embodiments, the concentration of soybean hydrolysate is 0.01-100 g/L. In some preferred embodiments, the concentration of soybean hydrolysate is 0.01, 0.05, 0.1, 0.25, 0.5, 0.75, 1, 5, 10, 15, 20, 25, 30, 35, 40, 45, 50, 55, 60, 65, 70, 75, 80, 85, 90, 95, or 100 g/L.

In some embodiments, the concentration of corn steep liquor is 0.25-100 g/L. In some preferred embodiments, the concentration of corn steep liquor is 0.25, 0.50, 0.75, 1, 5, 10, 15, 20, 25, 30, 35, 40, 45, 50, 55, 60, 65, 70, 75, 80, 85, 90, 95, or 100 g/L.

In some embodiments, the concentration of $MgSO_4.7H_2O$ is 0.1-2 g/L. In some preferred embodiments, the concentration of $MgSO_4.7H_2O$ is 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2 g/L.

In some embodiments, the concentration of $Al(NO_3)_3$ is 0.1-0.5 g/L. In some preferred embodiments, the concentration of $Al(NO_3)_3$ is 0.1, 0.2, 0.3, 0.4, or 0.5 g/L.

In some embodiments, the concentration of methanol is 1-5 mL/L. In some preferred embodiments, the concentration of methanol is 1, 1.1, 1.2, 1.3, 1.4, 1.5, 1.6, 1.7, 1.8, 1.9, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.95 mL/L.

In some embodiments, the microorganism is fermented at 25-50° C. In some preferred embodiments, the microorganism is fermented at 25, 26, 27, 28, 29, 30, 31, 32, 33, 34, 35, 36, 37, 38, 39, 40, 41, 42, 43, 44, 45, 46, 47, 48, 49, or 50° C.

In some embodiments, the microorganism is fermented in an environment of pH 4-9. In some preferred embodiments, the microorganism is fermented in an environment of pH 4, 4.5, 5, 5.5, 6, 6.5, 7, 7.5, 8, 8.5, or 9.

In some embodiments, the microorganism is fermented at 200-400 rpm. In some preferred embodiments, the microorganism is fermented at 200, 225, 250, 275, 300, 325, 350, 375, or 400 rpm.

In some embodiments, the microorganism is fermented for 48-240 hours. In some preferred embodiments, the microorganism is fermented for 48, 50, 55, 60, 65, 70, 75, 80, 85, 90, 95, 100, 110, 120, 130, 140, 150, 160, 170, 180, 190, 200, 210, 220, 230, or 240 hours.

As used herein, the singular forms "a", "an", and "the" include plural referents unless the context clearly dictates otherwise. Thus, for example, reference to "a component" includes a plurality of such components and equivalents thereof known to those skilled in the art. Moreover, titles or subtitles may be used in the specification for the convenience of a reader, which shall have no influence on the scope of the present invention.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The meaning of the technical and scientific terms as described herein can be clearly understood by a person of ordinary skill in the art.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views.

EXAMPLE 1

Effects of Pretreatment of Molasses on Fungal Growth

Molasses, a major by-product of the cane sugar industry, is dark-brown, thick liquid rich in nutrients. However, due to the equipment used in refining process of sugar cane, molasses stock is usually contaminated by a high amount of metal ions, which inhibits fungal growth and further reduces yields of glucosamine. Therefore, pretreatment of molasses stock may be important for glucosamine production, and in this Example, comparison of effects of untreated molasses stock and treated molasses on fungal growth was carried out.

I. Pretreatment of Molasses

Molasses stock was mixed with water at a ratio of 1:1 by volume, and the mixture was stirred until molasses stock was completely dissolved. The mixture was then stored at 4° C. to settle for 24 hours. After that, two layers were formed. The upper layer was a dark brown liquid, and the lower layer was brown mud. The volume ratio of the upper layer and the lower layer was about 9:1. The upper layer was collected as treated molasses and stored at 4° C.

II. Fungal Fermentation Test

*Aspergillus sydowii* BCRC 31742 (Hsinchu, Taiwan) was used in the tests of this Example. First, the fungi were recovered by being subcultured twice with the following method. *Aspergillus sydowii* BCRC 31742 was first cultured on $M_{300}Sb_5AlMeA$ solid-surface medium [300 mL/L (equivalent to about 163 g/L) of treated molasses, 5 mL/L (equivalent to about 2.81 g/L) of soybean hydrolysate, 0.1 g/L $MgSO_4.7H_2O$, 0.1 g/L $Al(NO_3)_3$, 1 mL/L methanol, and 20 g/L agar] by the three-sector streaking method to obtain isolated colonies at 30° C. for 7 days. An isolated colony of *Aspergillus sydowii* BCRC 31742 was then seeded in a 250 mL flask containing 150 mL of sterilized $M_{300}Sb_5AlMe$ liquid medium (300 mL/L treated molasses, 5 mL/L soybean hydrolysate, 0.1 g/L $MgSO_4.7H_2O$, 0.1 g/L $Al(NO_3)_3$, and 1 mL/L methanol) and incubated at 30° C., 200 rpm for 5 days.

After that, 15 mL of the recovered fungi were seeded in a 250 mL flask containing 150 mL of $M_{300}Sb_5AlMe$ liquid medium [300 mL/L molasses stock or treated molasses, 5 mL/L soybean hydrolysate, 0.1 g/L $MgSO_4.7H_2O$, 0.1 g/L $Al(NO_3)_3$, and 1 mL/L methanol, pH 7] and incubated at 30° C., 200 rpm. There were two types of $M_{300}Sb_5AlMe$ liquid medium in this Example. One contained untreated molasses stock, the other contained the treated molasses. The results indicate that fungi cannot grow in the medium containing untreated molasses stock, whereas fungi grow well in the medium containing the treated molasses (data not shown).

III. Analysis of Constituents of Molasses

Analyses of constituents of untreated molasses stock and the treated molasses were performed by Super Laboratory Co., Ltd. (New Taipei City, Taiwan). Results of the nutrition analyses are shown in Table 1, in which the treated molasses contains fewer metal ions than untreated molasses stock does. The results indicate that the pretreatment of molasses in the present invention effectively reduces the amount of metal ions in molasses stock, and therefore, solves the problem of inhibition of fungal growth by a high amount of metal ions in molasses stock. In addition, the treated molasses contains a proper amount of metal ions, which increase fungal growth and yields of glucosamine. The molasses mentioned in all of the rest Examples in the present invention refers to the treated molasses.

TABLE 1

Analyses of Constituents of Molasses Stock and Treated Molasses

| Items | Unit | Molasses Stock | Treated Molasses |
|---|---|---|---|
| Solid Contents | g/g of Solution | 0.82 | 0.46 |
| Solution Density | g/mL | 1.38 | 1.18 |

TABLE 1-continued

Analyses of Constituents of Molasses Stock and Treated Molasses

| Items | Unit | Molasses Stock | Treated Molasses |
|---|---|---|---|
| Calories | Kcal/100 g | 279 | 199 |
| Crude Protein | g/100 g | 6.80 | 4.70 |
| Fats | g/100 g | 0.70 | 1.40 |
| Saturated Fat | g/100 g | 0.06 | — |
| Trans Fat | g/100 g | — | — |
| Carbohydrates | g/100 g | 61.3 | 41.9 |
| Sugar | g/100 g | 39.1 | 29.0 |
| Fructose | g/100 g | 6.68 | 3.66 |
| Glucose | g/100 g | 2.44 | 1.45 |
| Sucrose | g/100 g | 29.7 | 23.9 |
| Maltose | g/100 g | 0.289 | — |
| Lactose | g/100 g | 0.055 | — |
| Metal Ions | | | |
| Sodium | mg/100 g | 70.2 | 45.7 |
| Potassium | mg/100 g | 2591 | 1631 |
| Iron | mg/100 g | 20.5 | 0.2 |
| Magnesium | mg/100 g | 384 | 290 |
| Phosphorus | mg/100 g | 50.1 | 2.73 |

EXAMPLE 2

Effects of Concentrations of Molasses on Fungal Growth

I. Fungal Fermentation Test

*Aspergillus sydowii* BCRC 31742 (Hsinchu, Taiwan) was also used in the tests of this Example. First, the fungi were recovered by being subcultured twice with the method described in Example 1.

After that, 15 mL of the recovered fungi were seeded in different flasks each containing 150 mL of the following media, respectively:

(1) $M_{200}Sb_5AlMe$ liquid medium [200 mL/L molasses (equivalent to about 110.8 g/L molasses), 5 mL/L soybean hydrolysate (equivalent to about 2.81 g/L soybean hydrolysate), 0.1 g/L $MgSO_4.7H_2O$, 0.1 g/L $Al(NO_3)_3$, and 1 mL/L methanol, pH 7]; and (2) $M_{300}Sb_5AlMe$ liquid medium [300 mL/L molasses (equivalent to about 163 g/L molasses), 5 mL/L soybean hydrolysate (equivalent to about 2.81 g/L soybean hydrolysate), 0.1 g/L $MgSO_4.7H_2O$, 0.1 g/L $Al(NO_3)_3$, and 1 mL/L methanol, pH 7]. The fungi were incubated at 30° C., 200 rpm for 5 days, and then were subject to determination of glucosamine.

II. Determination of Glucosamine

After the fungi were incubated for 5 days, cells were collected by vacuum filtration, dried at 60° C. to constant weights, and then weighed to obtain the biomass. One (1) gram of the dried cells was mixed with 10 mL of 6N HCl, and the mixture was incubated at 85° C. in a shaking water bath for 6 hours to obtain a liquid containing glucosamine. After the mixture was cooled to room temperature, 10 mL of deionized water was added, and the diluted mixture was neutralized to pH 7 with 10 N NaOH and then vacuum filtered to collect the filtrate. Zero point two (0.2) milliliter of the filtrate, 0.2 mL of 3,5-Dinitrobenzonitrile acetonitrile as the internal standard, and 0.6 mL of 40 mol/m³ 1-naphthyl isothiocyanate pyridine were mixed in a test tube and incubated at 50° C. in a shaking water bath for 1 hour. After that, 5 μL of the mixture was taken for determination of glucosamine.

High performance liquid chromatography (HPLC) was used to determine glucosamine. Conditions of HPLC are shown as follows.

HPLC pump: Shimadzu LC-20A;
Detector: Shimadzu Model SPD-10A UV-VIS index detector;
Column: Merck Purospher®STAR Rp-18 endcapped (5 μm), 250×4 mm I.D.;
Mobile phase: Water/Acetonitrile (85/15);
Flow rate: 1.1 mL/min; and
Wavelength of UV detector: 230nm.

The amount of glucosamine in the test sample was calculated by the following method. First, a calibration curve of glucosamine hydrochloride was created based on weight ratios and peak area ratios of glucosamine to different concentrations of the internal standard. Then, the peak area ratio of the glucosamine hydrochloride in the test sample to the internal standard in the test sample was substituted in the calibration curve to obtain the amount of glucosamine by interpolation method. Glucosamine concentration (gram of glucosamine/mL of medium) and glucosamine content (gram of glucosamine/gram of biomass) were calculated based on the obtained amounts of glucosamine. The results are shown in FIG. 1. The results indicate that when the concentration of molasses increased, both of the biomass of the fungi and the glucosamine content increased, and, therefore, the glucosamine concentration increased as well.

EXAMPLE 3

Effects of Concentrations of Aluminum Nitrate $(Al(NO_3)_3)$ on Fungal Growth

I. Fungal Fermentation Test

*Aspergillus sydowii* BCRC 31742 (Hsinchu, Taiwan) was also used in the tests of this Example. First, the fungi were recovered by being subcultured twice with the method described in Example 1.

After that, 15 mL of the recovered fungi were seeded in different flasks each containing 150 mL of the following media, respectively:

(1) $M_{300}Sb_5Me$ liquid medium [300 mL/L molasses (equivalent to about 163 g/L molasses), 5 mL/L soybean hydrolysate (equivalent to about 2.81 g/Lsoybean hydrolysate), 0.1 g/L $MgSO_4.7H_2O$, 0 g/L $Al(NO_3)_3$, 1 mL/L methanol, pH 7];
(2) $M_{300}Sb_5AlMe$ liquid medium [300 mL/L molasses (equivalent to about 163 g/L molasses), 5 mL/L soybean hydrolysate (equivalent to about 2.81 g/Lsoybean hydrolysate), 0.1 g/L $MgSO_4.7H_2O$, 0.1 g/L $Al(NO_3)_3$, 1 mL/L methanol, pH 7];
(3) $M_{300}Sb_5Al_2Me$ liquid medium [300 mL/L molasses (equivalent to about 163 g/L molasses), 5 mL/L soybean hydrolysate (equivalent to about 2.81 g/Lsoybean hydrolysate), 0.1 g/L $MgSO_4.7H_2O$, 0.2 g/L $Al(NO_3)_3$, 1 mL/L methanol, pH 7];
(4) $M_{300}Sb_5Al_4Me$ liquid medium [300 mL/L molasses (equivalent to about 163 g/L molasses), 5 mL/L soybean hydrolysate (equivalent to about 2.81 g/Lsoybean hydrolysate), 0.1 g/L $MgSO_4.7H_2O$, 0.4 g/L $Al(NO_3)_3$, 1 mL/L methanol, pH 7];
(5) $M_{300}Sb_5Al_5Me$ liquid medium [300 mL/L molasses (equivalent to about 163 g/L molasses), 5 mL/L soybean hydrolysate (equivalent to about 2.81 g/Lsoybean hydrolysate), 0.1 g/L $MgSO_4.7H_2O$, 0.5 g/L $Al(NO_3)_3$, 1 mL/L methanol, pH 7]; and
(6) $M_{300}Sb_5Al_{10}Me$ liquid medium [300 mL/L molasses (equivalent to about 163 g/L molasses), 5 mL/L soybean hydrolysate (equivalent to about 2.81 g/Lsoybean hydrolysate), 0.1 g/L $MgSO_4.7H_2O$, 1 g/L $Al(NO_3)_3$, 1 mL/L methanol, pH 7];

The fungi were incubated at 30° C., 200 rpm for 5 days, and then were subject to determination of glucosamine.

II. Determination of Glucosamine

Figure 2:
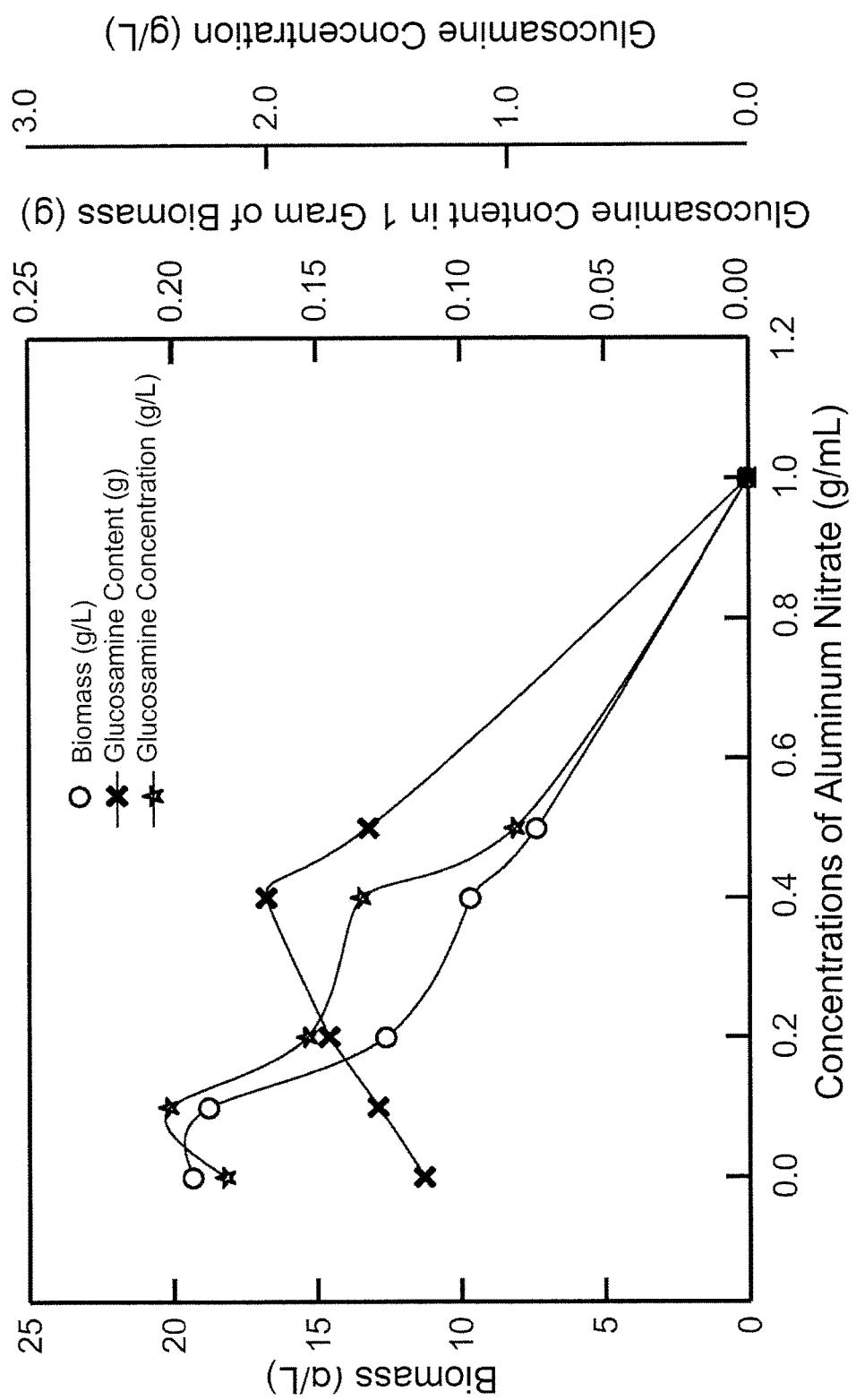
FIG. 2 shows the biomass, glucosamine concentration, and glucosamine content of *Aspergillus sydowii* BCRC 31742 cultivated in media containing different concentrations of aluminum nitrate in shake flasks.

Treatment of the fungi and analysis method and conditions of HPLC are the same as those described in Example 2. The results of biomass, glucosamine content (gram of glucosamine/gram of biomass), and glucosamine concentration (gram of glucosamine/L of medium) are shown in FIG. 2.

The results indicate that trace amounts of aluminum nitrate effectively increased the glucosamine concentration. However, when the concentration of aluminum nitrate increased, both of the biomass of the fungi and the glucosamine concentration decreased. Therefore, in order to optimize the yields of glucosamine, the concentration of aluminum nitrate in the medium is preferably between 0.1-0.5 g/L, and is most preferably 0.1 g/L, where the glucosamine concentration reached to the highest level.

EXAMPLE 4

Effects of Concentrations of Methanol on Fungal Growth

I. Fungal Fermentation Test

*Aspergillus sydowii* BCRC 31742 (Hsinchu, Taiwan) was also used in the tests of this Example. First, the fungi were recovered by being subcultured twice with the method described in Example 1.

After that, 15 mL of the recovered fungi were seeded in different flasks each containing 150 mL of the following media, respectively:

(1) $M_{300}Sb_5Al$ liquid medium [300 mL/L molasses (equivalent to about 163 g/L molasses), 5 mL/L soybean hydrolysate (equivalent to about 2.81 g/Lsoybean hydrolysate), 0.1 g/L $MgSO_4.7H_2O$, 0.1 g/L $Al(NO_3)_3$, 0 mL/L methanol, pH 7];
(2) $M_{300}Sb_5AlMe$ liquid medium [300 mL/L molasses (equivalent to about 163 g/L molasses), 5 mL/L soybean hydrolysate (equivalent to about 2.81 g/Lsoybean hydrolysate), 0.1 g/L $MgSO_4.7H_2O$, 0.1 g/L $Al(NO_3)_3$, 1 mL/L methanol, pH 7];
(3) $M_{300}Sb_5AlMe_2$ liquid medium [300 mL/L molasses (equivalent to about 163 g/L molasses), 5 mL/L soybean hydrolysate (equivalent to about 2.81 g/Lsoybean hydrolysate), 0.1 g/L $MgSO_4.7H_2O$, 0.1 g/L $A1(NO_3)_3$, 2 mL/L methanol, pH 7];
(4) $M_{300}Sb_5AlMe_5$ liquid medium [300 mL/L molasses (equivalent to about 163 g/L molasses), 5 mL/L soybean hydrolysate (equivalent to about 2.81 g/Lsoybean hydrolysate), 0.1 g/L $MgSO_4.7H_2O$, 0.1 g/L $Al(NO_3)_3$, 5 mL/L methanol, pH 7];
(5) $M_{300}Sb_5AlMe_{10}$ liquid medium [300 mL/L molasses (equivalent to about 163 g/L molasses), 5 mL/L soybean hydrolysate (equivalent to about 2.81 g/Lsoybean hydrolysate), 0.1 g/L $MgSO_4.7H_2O$, 0.1 g/L $Al(NO_3)_3$, 10 mL/L methanol, pH 7];

The fungi were incubated at 30° C., 200 rpm for 5 days, and then were subject to determination of glucosamine.

II. Determination of Glucosamine

Figure 3:
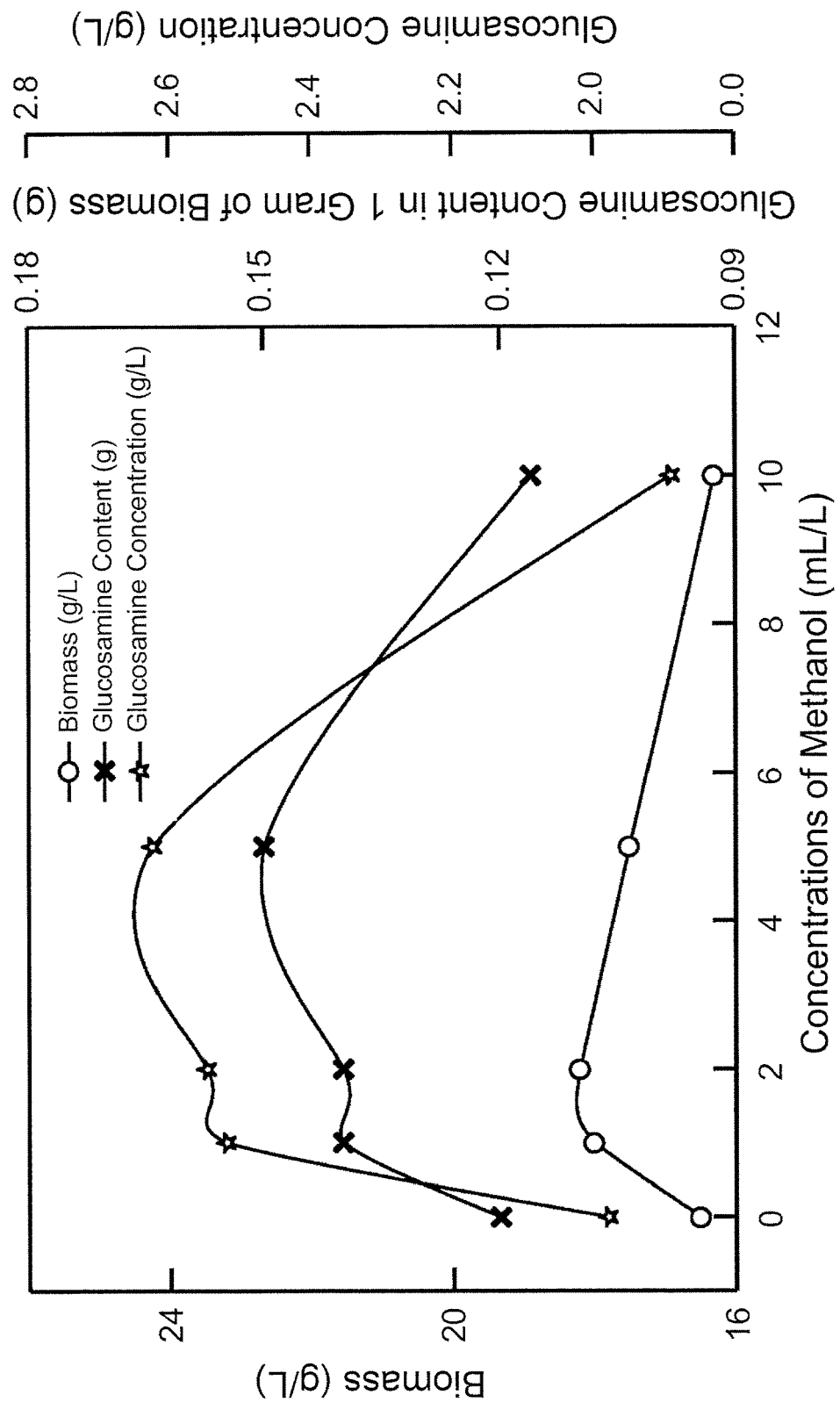
FIG. 3 shows the biomass, glucosamine concentration, and glucosamine content of *Aspergillus sydowii* BCRC 31742 cultivated in media containing different concentrations of methanol in shake flasks.

Treatment of the fungi and analysis method and conditions of HPLC are the same as those described in Example 2. The results of biomass, glucosamine content (gram of glucosamine/gram of biomass), and glucosamine concentration (gram of glucosamine/L of medium) are shown in FIG. 3.

The results indicate that trace amounts of methanol effectively increased the glucosamine concentration. However, when the concentration of methanol increased, both of the biomass of the fungi and the glucosamine concentration decreased. When the concentration of methanol reached to 10 mL/L (1%), fungal growth was inhibited. Therefore, in order to optimize the yields of glucosamine, the concentration of methanol in the medium is preferably between 1-5 mL/L.

EXAMPLE 5

Effects of Medium Composition on Fungal Growth

I. Fungal Fermentation Test

*Aspergillus sydowii* BCRC 31742 (Hsinchu, Taiwan) was also used in the tests of this Example. First, the fungi were recovered by being subcultured twice with the method described in Example 1.

After that, 15 mL of the recovered fungi were seeded in different flasks each containing 150 mL of the following media, respectively:
(1) $M_{300}Sb_5$ liquid medium [300 mL/L molasses (equivalent to about 163 g/L molasses), 5 mL/L soybean hydrolysate (equivalent to about 2.81 g/L soybean hydrolysate), 0.1 g/L $MgSO_4.7H_2O$, pH 7];
(2) $M_{300}Sb_5Al$ liquid medium [300 mL/L molasses (equivalent to about 163 g/L molasses), 5 mL/L soybean hydrolysate (equivalent to about 2.81 g/L soybean hydrolysate), 0.1 g/L $MgSO_4.7H_2O$, 0.1 g/L $Al(NO_3)_3$, pH 7];
(3) $M_{300}Sb_5Me$ liquid medium [300 mL/L molasses (equivalent to about 163 g/L molasses), 5 mL/L soybean hydrolysate (equivalent to about 2.81 g/L soybean hydrolysate), 0.1 g/L $MgSO_4.7H_2O$, 1 mL/L methanol, pH 7];
(4) $M_{300}Sb_5AlMe$ liquid medium [300 mL/L molasses (equivalent to about 163 g/L molasses), 5 mL/L soybean hydrolysate (equivalent to about 2.81 g/L soybean hydrolysate), 0.1 g/L $MgSO_4.7H_2O$, 0.1 g/L $Al(NO_3)_3$, 1 mL/L methanol, pH 7];
The fungi were incubated at 30° C., 200 rpm for 5 days, and then were subject to determination of glucosamine.

II. Determination of Glucosamine

Figure 4:
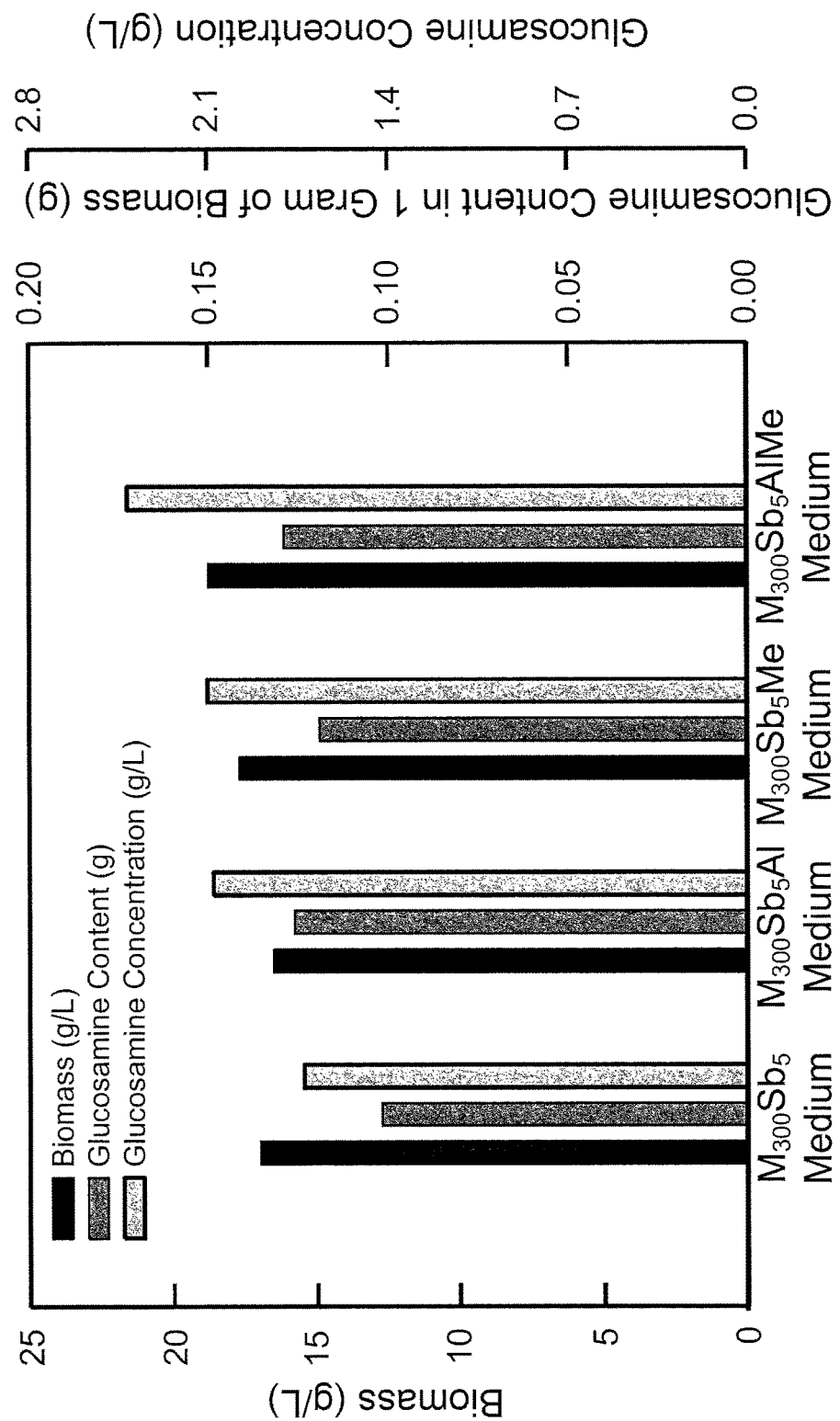
FIG. 4 shows the biomass, glucosamine concentration, and glucosamine content of *Aspergillus sydowii* BCRC 31742 cultivated in different media in shake flasks.

Treatment of the fungi and analysis method and conditions of HPLC are the same as those described in Example 2. The results of biomass, glucosamine content (gram of glucosamine/gram of biomass), and glucosamine concentration (gram of glucosamine/L of medium) are shown in FIG. 4.

In this Example, fungi cultivated in $M_{300}Sb_5AlMe$ liquid medium [300 mL/L molasses (equivalent to about 163 g/L molasses), 5 mL/L soybean hydrolysate (equivalent to about 2.81 g/L soybean hydrolysate), 0.1 g/L $MgSO_4.7H_2O$, 0.1 g/L $Al(NO_3)_3$, 1 mL/L methanol] produced the most biomass and the highest glucosamine concentration.

EXAMPLE 6

Effects of Medium Composition on Fungal Growth in Shake-Flask Culture

I. Fungal Fermentation Test

*Absidia coerulea* BCRC32931 (Hsinchu, Taiwan), *Aspergillus sydowii* BCRC 31742 (Hsinchu, Taiwan), and *Mucor indicus* BCRC32158 (Hsinchu, Taiwan) were used in the tests of this Example. First, the fungi were recovered by being subcultured twice with the method described in Example 1.

After that, 15 mL of the recovered fungi were seeded in different flasks each containing 150 mL of the following media, respectively:
(1) $M_{300}Sb_5AlMe$ liquid medium [300 mL/L molasses (equivalent to about 163 g/L molasses), 5 mL/L soybean hydrolysate (equivalent to about 2.81 g/L soybean hydrolysate), 0.1 g/L $MgSO_4.7H_2O$, 0.1 g/L $Al(NO_3)_3$, 1 mL/L methanol, pH 7];
(2) GP liquid medium (33.9 g/L glucose, 40.6 g/L mycological-peptone, 0.5 g/L $MgSO_4.7H_2O$, 0.5 g/L $KH_2PO_4$, 0.1 g/L $CaCl_2$);
(3) WF liquid medium (33.9 g/L white fine-granulated sugar, 40.6 g/L mycological-peptone, 0.5 g/L $MgSO_4.7H_2O$, 0.5 g/L $KH_2PO_4$, 0.1 g/L $CaCl_2$);
(4) YPG liquid medium [20 g/L glucose, 10 g/L mycological-peptone, 1 g/L yeast extract, 1 g/L $(NH_4)_2SO_4$, 1 g/L NaCl, 0.5 g/L $MgSO_4.7H_2O$, 0.1 g/L $CaCl_2$];
The fungi were incubated at 30° C., 200 rpm for 5 days, and then were subject to determination of glucosamine.

II. Determination of Glucosamine

Treatment of the fungi and analysis method and conditions of HPLC are the same as those described in Example 2. The results of biomass, glucosamine content (gram of glucosamine/gram of biomass), glucosamine concentration (gram of glucosamine/L of medium), yields based on carbon source in fermentation medium, and productivities based on working days are shown in Table 2.

As shown in Table 2, comparing to being cultivated in WF medium or YPG medium, all the three fungi cultivated in $M_{300}Sb_5AlMe$ liquid medium produced the same amounts of glucosamine with the lowest production costs. In addition, among the three fungi, *Aspergillus sydowii*. BCRC 31742 cultivated in $M_{300}Sb_5AlMe$ liquid medium produced glucosamine with the lowest production cost (358.6 NTD/kg-glucosamine).

TABLE 2

Comparison of glucosamine concentrations, glucosamine content, productivities, and production costs of three fungi cultivated in different media in shake flasks.

| Fungus Strain | Medium | Biomass (g/L) | glucosamine concentration (g glucosamine/ L) | glucosamine content (g glucosamine/ g biomass) | productivity (g/L · h) | Production cost (NTD/kg glucosamine) |
|---|---|---|---|---|---|---|
| *Absidia coerulea* BCRC32931 | $M_{300}Sb_5AlMe$ | 14.5 | 1.09 | 0.075 | 11.3 | 865.1 |
| | WF | 15.28 | 1.86 | 0.120 | 15.49 | 51734 |
| | YPG | 9.86 | 1.55 | 0.160 | 12.93 | 44458 |
| *Aspergillus sydowii* BCRC31742 | $M_{300}Sb_5AlMe$ | 21.8 | 2.63 | 0.120 | 15.6 | 359 |
| | GP | 18.5 | 3.42 | 0.185 | 20.4 | 60450 |
| | WF | 28.7 | 7.48 | 0.261 | 62.3 | 12864 |

TABLE 2-continued

Comparison of glucosamine concentrations, glucosamine content, productivities, and production costs of three fungi cultivated in different media in shake flasks.

| Fungus Strain | Medium | Biomass (g/L) | glucosamine concentration (g glucosamine/ L) | glucosamine content (g glucosamine/ g biomass) | productivity (g/L · h) | Production cost (NTD/kg glucosamine) |
|---|---|---|---|---|---|---|
| Mucor indicus BCRC32158 | $M_{300}Sb_5AlMe$ | 14 | 1.14 | 0.082 | 11.9 | 827.2 |
| | WF | 15.85 | 1.79 | 0.110 | 14.94 | 53758 |
| | YPG | 6.93 | 1.31 | 0.190 | 10.94 | 52603 |

EXAMPLE 7

Effects of Rotation Speeds on Fungal Growth in a Fermenter

I. Fungal Fermentation Test

Aspergillus sydowii BCRC 31742 (Hsinchu, Taiwan) was also used in the tests of this Example. First, the fungi were recovered by being subcultured twice with the method described in Example 1.

After that, 300 mL of the recovered fungi were seeded in mechanical agitation fermenters each containing 3L of $M_{300}Sb_5AlMe$ liquid medium [300 mL/L molasses (equivalent to about 163 g/L molasses), 5 mL/L soybean hydrolysate (equivalent to about 2.81 g/L soybean hydrolysate), 0.1 g/L $MgSO_4.7H_2O$, 0.1 g/L $Al(NO_3)_3$, 1 mL/L methanol, pH 7]. The fungi were incubated at 30° C. and at different ration speeds, which are 200, 300, and 400 rpm, respectively, for 5 days with air supply through a pipe, and then were subject to determination of glucosamine.

II. Determination of Glucosamine

Figure 5:
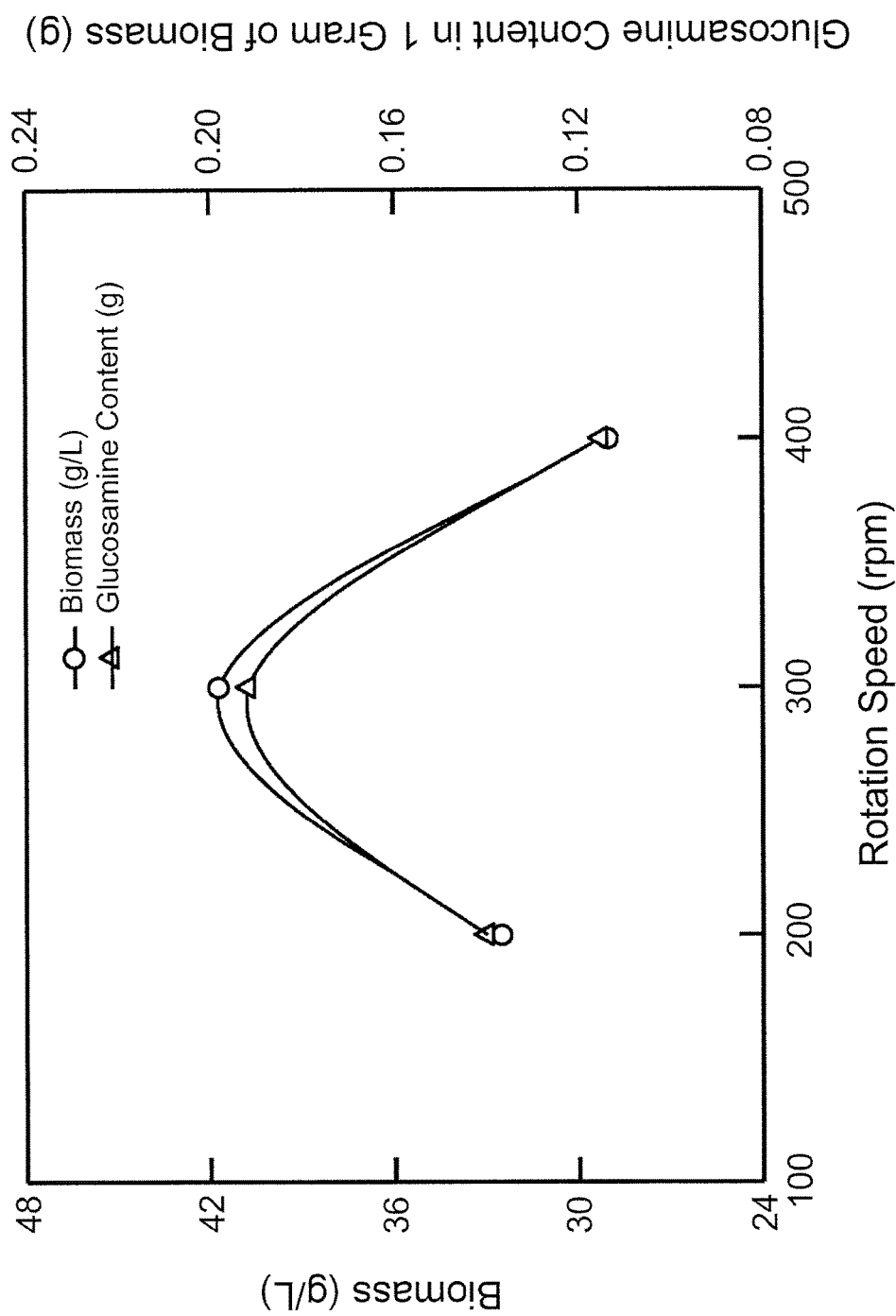
FIG. 5 shows the biomass and glucosamine content of *Aspergillus sydowii* BCRC 31742 cultivated in fermenters at different rotation speeds.

Treatment of the fungi and analysis method and conditions of HPLC are the same as those described in Example 2. The results of biomass, glucosamine content (gram of glucosamine/gram of biomass), and glucosamine concentration (gram of glucosamine/L of medium) are shown in FIG. 5.

The results indicate that fungi cultivated at 300 rpm in fermenters produced the most biomass and the highest glucosamine concentration. In contrast, fungi cultivated at 200 rpm in fermenters grew too slowly to produce enough biomass due to inadequate aeration caused by the low rotation speed. In addition, fungi cultivated at 400 rpm in fermenters also grew too slowly to produce enough biomass due to broken fungus caused by the high rotation speed.

EXAMPLE 8

Effects of Different Media on Fungal Growth in a Fermenter

I. Fungal Fermentation Test

Aspergillus sydowii BCRC 31742 (Hsinchu, Taiwan) was also used in the tests of this Example. First, the fungi were recovered by being subcultured twice with the method described in Example 1.

After that, 300 mL of the recovered fungi were seeded in different mechanical agitation fermenters each containing 3L of the following media, respectively:

(1) $M_{300}Sb_5AlMe$ liquid medium [300 mL/L molasses (equivalent to about 163 g/L molasses), 5 mL/L soybean hydrolysate (equivalent to about 2.81 g/L soybean hydrolysate), 0.1 g/L $MgSO_4.7H_2O$, 0.1 g/L $Al(NO_3)3$, 1 mL/L methanol, pH 7];

(2) GP liquid medium (33.9 g/L glucose, 40.6 g/L mycological-peptone, 0.5 g/L $MgSO_4.7H_2O$, 0.5 g/L $KH_2PO_4$, 0.1 g/L $CaCl_2$);

(3) WF liquid medium (20 g/L glucose, 10 g/L mycological-peptone, 1 g/L yeast extract, 1 g/L $(NH_4)2SO_4$, 1 g/L NaCl, 0.5 g/L $MgSO_4.7H_2O$, 0.1 g/L $CaCl_2$);

The fungi were incubated at 30° C., 300 rpm for 5 days with air supply through a pipe, and then were subject to determination of glucosamine.

II. Determination of Glucosamine

Treatment of the fungi and analysis method and conditions of HPLC are the same as those described in Example 2. The results of biomass, glucosamine content (gram of glucosamine/gram of biomass), glucosamine concentration (gram of glucosamine/L of medium), yields based on carbon source in fermentation medium, and productivities based on working days are shown in Table 3.

As shown in Table 3, among all the three media used in this Example, fungi cultivated in $M_{300}Sb_5AlMe$ liquid medium produced glucosamine with the lowest production costs, which was less than 1% of the production costs of glucosamine produced by fungi cultivated in the other two media. Therefore, the present invention provides a medium containing molasses suitable for mass production of glucosamine to reduce production costs.

TABLE 3

Comparison of glucosamine concentrations, glucosamine content, productivities, and production costs of fungi cultivated in different media in fermenters.

| Fungus Strain | Medium | Biomass (g/L) | glucosamine concentration (g glucosamine/ L) | glucosamine content (g glucosamine/ g biomass) | productivity (g/L · h) | Production cost (NTD/kg glucosamine) |
|---|---|---|---|---|---|---|
| Aspergillus sydowii BCRC31742 | $M_{300}Sb_5AlMe$ | 41.7 | 7.17 | 0.172 | 74.7 | 131.5 |
| | GP | 41.3 | 13.5 | 0.327 | 242 | 15314.1 |
| | WF | 32.1 | 5.61 | 0.175 | 46.8 | 17152.8 |

EXAMPLE 9

Effects of Different Nitrogen Sources on Fungal Growth

I. Fungal Fermentation Test

*Aspergillus sydowii* BCRC 31742 (Hsinchu, Taiwan) was also used in the tests of this Example. First, the fungi were recovered by being subcultured twice with the method described in Example 1.

After that, 15 mL of the recovered fungi were seeded in different flasks each containing 150 mL of the following media, respectively:
(1) $M_{300}Sb_5$ liquid medium [300 mL/L molasses (equivalent to about 163 g/L molasses), 5 mL/L soybean hydrolysate (equivalent to about 2.81 g/L soybean hydrolysate), 0.1 g/L $MgSO_4 \cdot 7H_2O$, pH 7];
(2) $M_{300}Sb_5Me$ liquid medium [300 mL/L molasses (equivalent to about 163 g/L molasses), 5 mL/L soybean hydrolysate (equivalent to about 2.81 g/L soybean hydrolysate), 0.1 g/L $MgSO_4 \cdot 7H_2O$, 1 mL/L methanol, pH 7];
(3) $M_{300}C_{20}Me$ liquid medium [300 mL/L molasses (equivalent to about 163 g/L molasses), 20 mL/L corn steep liquor (equivalent to about 7.6 g/L), 1 mL/L methanol, pH 7];

The fungi were incubated at 30° C., 200 rpm for 5 days, and then were subject to determination of glucosamine.

In this Example, soybean hydrolysate and corn steep liquor were used as two different nitrogen sources, whose analyses of composition are shown in Table 4.

TABLE 4

Analyses of Composition of Soybean Hydrolysate and Corn Steep Liquor

| Items | Unit | Soybean Hydrolysate | Corn Steep Liquor |
|---|---|---|---|
| Solid Contents | g/g of Solution | 0.46 | 0.34 |
| Solution Density | g/mL | 1.22 | 1.12 |
| Alanine | mg/100 g | 23.96 | 72.25 |
| Glycine | mg/100 g | 23.52 | 43.84 |
| Valine | mg/100 g | 23.85 | 45.11 |
| Leucine | mg/100 g | 43.78 | 113.53 |
| Isoleucine | mg/100 g | 24.36 | 32.24 |
| Proline | mg/100 g | 30.07 | 108.32 |
| Glutamic acid | mg/100 g | 109.09 | 198.65 |
| Methionine | mg/100 g | 7.42 | 27.13 |
| Asparagine | mg/100 g | 65.14 | 61.92 |
| Hydroxyproline | mg/100 g | — | — |
| Phenylalanine | mg/100 g | 27.62 | 55.43 |
| Cysteine | mg/100 g | 6.81 | 47.67 |
| Lysine | mg/100 g | 34.18 | 61.92 |
| Histidine | mg/100 g | 14.22 | 39.05 |
| Tyrosine | mg/100 g | 21.36 | 28.41 |
| Serine | mg/100 g | 29.38 | 50.33 |
| Threonine | mg/100 g | 21.99 | 23.20 |

II. Determination of Glucosamine

Figure 6:
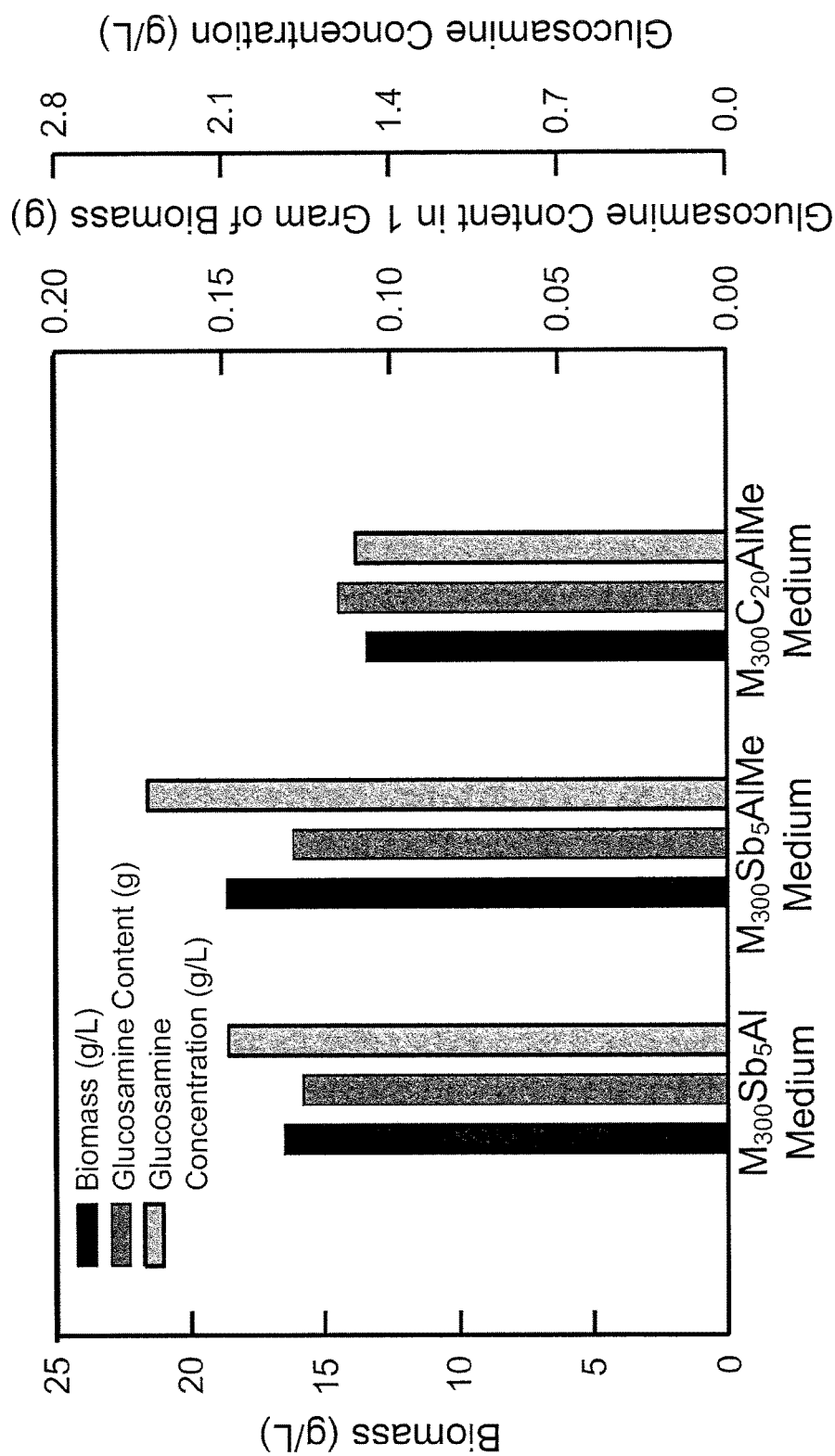
FIG. 6 shows the biomass, glucosamine concentration, and glucosamine content of *Aspergillus sydowii* BCRC 31742 cultivated in media containing different nitrogen sources in shake flasks.

Treatment of the fungi and analysis method and conditions of HPLC are the same as those described in Example 2. The results of biomass, glucosamine content (gram of glucosamine/gram of biomass), and glucosamine concentration (gram of glucosamine/L of medium) are shown in FIG. 6.

As shown in Table 5, when soybean hydorlysate was replaced by corn steep liquor as the nitrogen source in medium, the fungi produced less biomass but higher glucosamine content, which means more glucosamine in one gram of biomass. In addition, using corn steep liquor as the nitrogen source in medium reduces production costs of glucosamine, which are lower than the production costs of glucosamine produced with medium containing soybean hydorlysate as the nitrogen source. The results indicate that corn steep liquor is also an ideal nitrogen source for fungi to produce glucosamine.

TABLE 5

Comparison of glucosamine concentrations, glucosamine content, productivities, and production costs of *Aspergillus sydowii* cultivated in different media in shake flasks.

| Fungus Strain | Medium | Biomass (g/L) | glucosamine concentration (g glucosamine/ L) | glucosamine content (g glucosamine/ g biomass) | productivity (g/L · h) | Production cost (NTD/kg glucosamine) |
|---|---|---|---|---|---|---|
| *Aspergillus sydowii* BCRC31742 | $M_{300}Sb_5AlMe$ | 21.8 | 2.63 | 0.120 | 15.6 | 359 |
| | $M_{300}C_{20}AlMe$ | 13.4 | 1.55 | 0.115 | 13.0 | 354 |
| | GP | 18.5 | 3.42 | 0.185 | 20.4 | 60450 |
| | WF | 28.7 | 7.48 | 0.261 | 62.3 | 12864 |

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments are chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, to promote the progress in science and the useful arts, the scope of the present invention is disclosed and is intended to be limited only defined by the scope of the appended claims rather than the foregoing description and the exemplary embodiments described therein.

What is claimed is:

1. A method for producing glucosamine, comprising: providing a microorganism being able to produce glucosamine, and the microorganism is selected from the group consisting of *Absidia coerulea* BCRC32931, *Aspergillus sydowii* BCRC31742, and *Mucor indicus* BCRC32158; and
fermenting the microorganism in a medium comprising:
100-200 g/L treated molasses;
a nitrogen source selected from the group consisting of 1-10 g/L soybean hydrolysate and 1-10 g/L corn steep liquor;
0.1 g/L MgSO$_4$7H$_2$O;
0.1-0.5 g/L A;(NO$_3$)$_3$; and 1-5 mL/L methanol,
wherein the molasses is pretreated with the following steps:
mixing a molasses stock with water at a ratio of 1:1 by volume;
allowing the mixed molasses stock and water to settle at 4° C. for 24 hours and form an upper layer and a lower layer; and
collecting the upper layer as the treated molasses,
wherein the microorganism is fermented at 30° C.;
wherein the microorganism is fermented in an environment of pH 4-9;
wherein the microorganism is fermented at 300 rpm; and
wherein the microorganism is fermented for 48-240 hours.

\* \* \* \* \*